(12) United States Patent
Chen

(10) Patent No.: US 11,559,256 B2
(45) Date of Patent: Jan. 24, 2023

(54) METHOD AND APPARATUS FOR DETECTING WEARABLE DEVICE'S CONTACT WITH LIVING BODY

(71) Applicant: Nokia Technologies Oy, Espoo (FI)

(72) Inventor: Yue Chen, Beijing (CN)

(73) Assignee: Nokia Technologies Oy, Espoo (FI)

( * ) Notice: Subject to any disclaimer, the term of this patent is extended or adjusted under 35 U.S.C. 154(b) by 1085 days.

(21) Appl. No.: 16/307,216

(22) PCT Filed: Jun. 12, 2016

(86) PCT No.: PCT/CN2016/085472
§ 371 (c)(1),
(2) Date: Dec. 5, 2018

(87) PCT Pub. No.: WO2017/214772
PCT Pub. Date: Dec. 12, 2017

(65) Prior Publication Data
US 2019/0290205 A1    Sep. 26, 2019

(51) Int. Cl.
*A61B 5/00* (2006.01)
*A61B 5/01* (2006.01)

(52) U.S. Cl.
CPC .......... *A61B 5/6843* (2013.01); *A61B 5/0008* (2013.01); *A61B 5/01* (2013.01); *A61B 5/6885* (2013.01); *A61B 5/746* (2013.01); *A61B 2560/0242* (2013.01); *A61B 2560/0252* (2013.01); *A61B 2562/0271* (2013.01)

(58) Field of Classification Search
CPC ....... A61B 5/6843; A61B 5/0008; A61B 5/01; A61B 5/6885; A61B 5/746; A61B 2560/0242; A61B 2560/0252; A61B 2562/0271; G01K 3/10; G01K 13/20
See application file for complete search history.

(56) References Cited

U.S. PATENT DOCUMENTS

| | | | |
|---|---|---|---|
| 5,732,711 A | 3/1998 | Fitzpatrick et al. | 128/736 |
| 7,410,291 B2 * | 8/2008 | Koch | G01K 7/42 |
| | | | 374/102 |
| 2006/0173375 A1 | 8/2006 | Koch | 600/549 |
| 2007/0038141 A1 | 2/2007 | Koch | 600/549 |
| 2013/0072765 A1 * | 3/2013 | Kahn | G16H 50/20 |
| | | | 600/301 |

(Continued)

FOREIGN PATENT DOCUMENTS

| | | |
|---|---|---|
| CN | 101246532 A | 8/2008 |
| CN | 104665820 A | 6/2015 |

(Continued)

*Primary Examiner* — Quan Zhen Wang
*Assistant Examiner* — Rajsheed O Black-Childress
(74) *Attorney, Agent, or Firm* — Harrington & Smith

(57) ABSTRACT

A method for detecting a wearable device's contact with a living body may be provided, including obtaining a decreasing rate of body temperature and a decreasing a rate of environmental temperature measured by a wearable device worn on a living body; and determining the wearable device's contact with the living body based on a comparison of the decreasing rate of body temperature and the decreasing rate of environmental temperature. A corresponding apparatus and computer program product for detecting a wearable device's contact with a living body may also be provided.

12 Claims, 5 Drawing Sheets

(56) References Cited

U.S. PATENT DOCUMENTS

2016/0162256 A1\* 6/2016 Komaromi ............... H04Q 9/00
340/870.07

FOREIGN PATENT DOCUMENTS

| CN | 205041401 U | 2/2016 |
|---|---|---|
| CN | 105387945 A | 3/2016 |
| EP | 0 778 000 A1 | 6/1997 |
| EP | 2 243 422 A1 | 10/2010 |
| EP | 2 851 001 A2 | 3/2015 |

\* cited by examiner

METHOD AND APPARATUS FOR DETECTING WEARABLE DEVICE'S CONTACT WITH LIVING BODY

This patent application is a U.S. National Stage application of International Patent Application Number PCT/CN2016/085472 filed Jun. 12, 2016, which is hereby incorporated by reference in its entirety.

TECHNICAL FIELD

Embodiments of the present invention relate generally to wearable devices, more particularly, relate to a method and apparatus for detecting a wearable device's contact with a living body.

BACKGROUND

Temperature is an important index of human health. If somebody's temperature is out of a normal scope such as 36.5-37.5° C., that probably means an illness such as a flu, therefore people are used to measure body temperature for auto diagnosis. There are several ways to measure body temperature, for example, detecting human internal temperature such as that in the mouth, rectum or vagina etc. or detecting tympanic temperature such as that in the ear, however the most popular and convenient way is detecting skin temperature such as that of forehead or under the arm. The traditional thermometer to measure skin temperature such as that under the arm is a mercury thermometer which has been used for centuries and recently replaced by modern thermometers such as a wearable thermometer which can be adhered to skin in order to acquire skin temperature, and transfer temperature data directly to a receiving device such as a smartphone through wireless connections such as Bluetooth, WiFi etc.

Compared to traditional mercury thermometers, a wearable thermometer has several advantages:

1. A wearable thermometer can be put onto any part of human body such as chest or abdomen, whereas a mercury thermometer requires to be held tightly under the arm.
2. A wearable thermometer can continuously monitor temperature, for example, during sleep at night, and transfer temperature data to a receiving device such as a smart phone, iPad etc.

BRIEF SUMMARY

A method, apparatus and computer program product are therefore provided which may enable detecting a wearable device's contact with a living body. In this regard, example embodiments of the present invention may obtain a decreasing rate of body temperature and a decreasing a rate of environmental temperature measured by a wearable device worn on a living body. Various embodiments may also determine the wearable device's contact with the living body based on a comparison of the decreasing rate of body temperature and the decreasing rate of environmental temperature.

In one example embodiment, a method for detecting a wearable device's contact with a living body is described. The method may include obtaining a decreasing rate of body temperature and a decreasing a rate of environmental temperature measured by a wearable device worn on a living body. The method may further include determining the wearable device's contact with the living body based on a comparison of the decreasing rate of body temperature and the decreasing rate of environmental temperature.

In another example embodiment, an apparatus for detecting a wearable device's contact with a living body is described. The apparatus may include at least one processor, and at least one memory including computer program code. The at least one memory and the computer program code may be configured to, with the at least one processor, cause the apparatus at least to obtain a decreasing rate of body temperature and a decreasing a rate of environmental temperature measured by a wearable device worn on a living body. The at least one memory and the computer program code may be further configured to, with the at least one processor, cause the apparatus at least to determine the wearable device's contact with the living body based on a comparison of the decreasing rate of body temperature and the decreasing rate of environmental temperature.

In another example embodiment, a computer program product for detecting a wearable device's contact with a living body is described. The computer program product may include at least one computer-readable storage medium having computer-readable program code portions stored therein. The computer-readable program code portions may include first and second. The first program code portion may be configured to obtain a decreasing rate of body temperature and a decreasing a rate of environmental temperature measured by a wearable device worn on a living body. The second program code portion may be configured to determine the wearable device's contact with the living body based on a comparison of the decreasing rate of body temperature and the decreasing rate of environmental temperature.

BRIEF DESCRIPTION OF THE DRAWING(S)

Having thus described the invention in general terms, reference will now be made to the accompanying drawings, which are not necessarily drawn to scale, and wherein:

Figure 4:
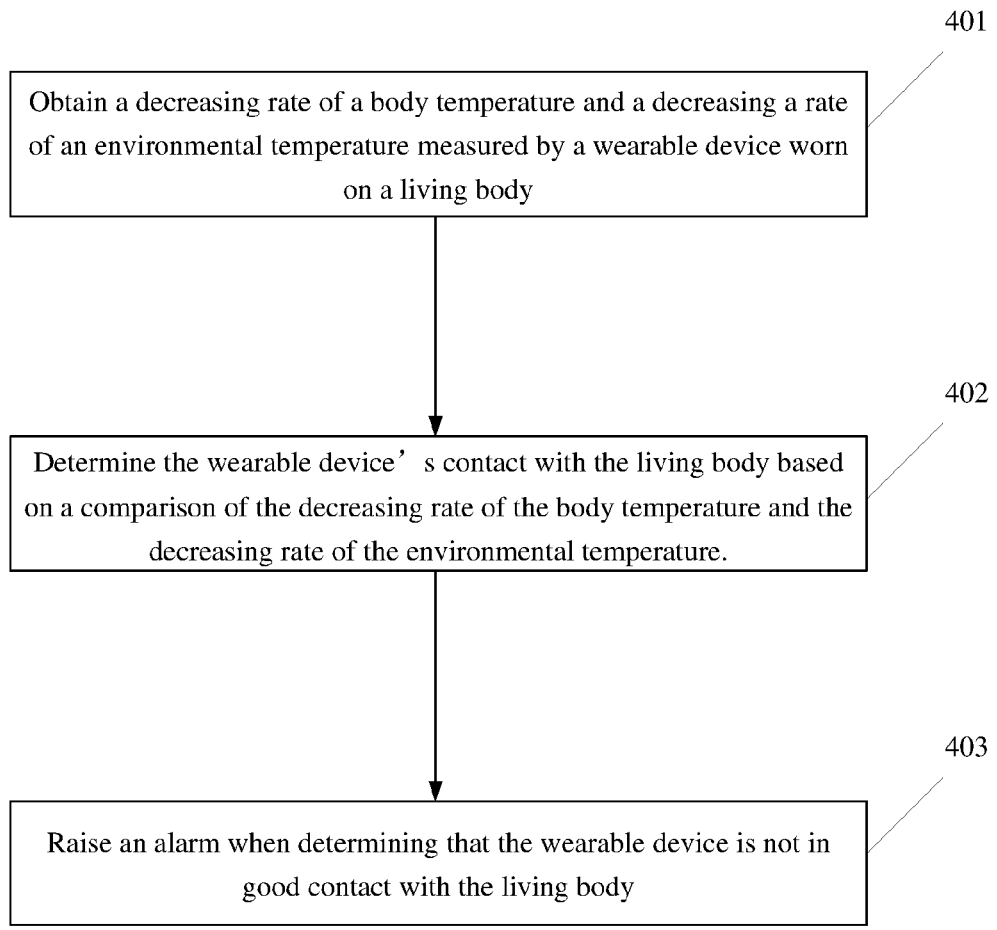
Figure 5:
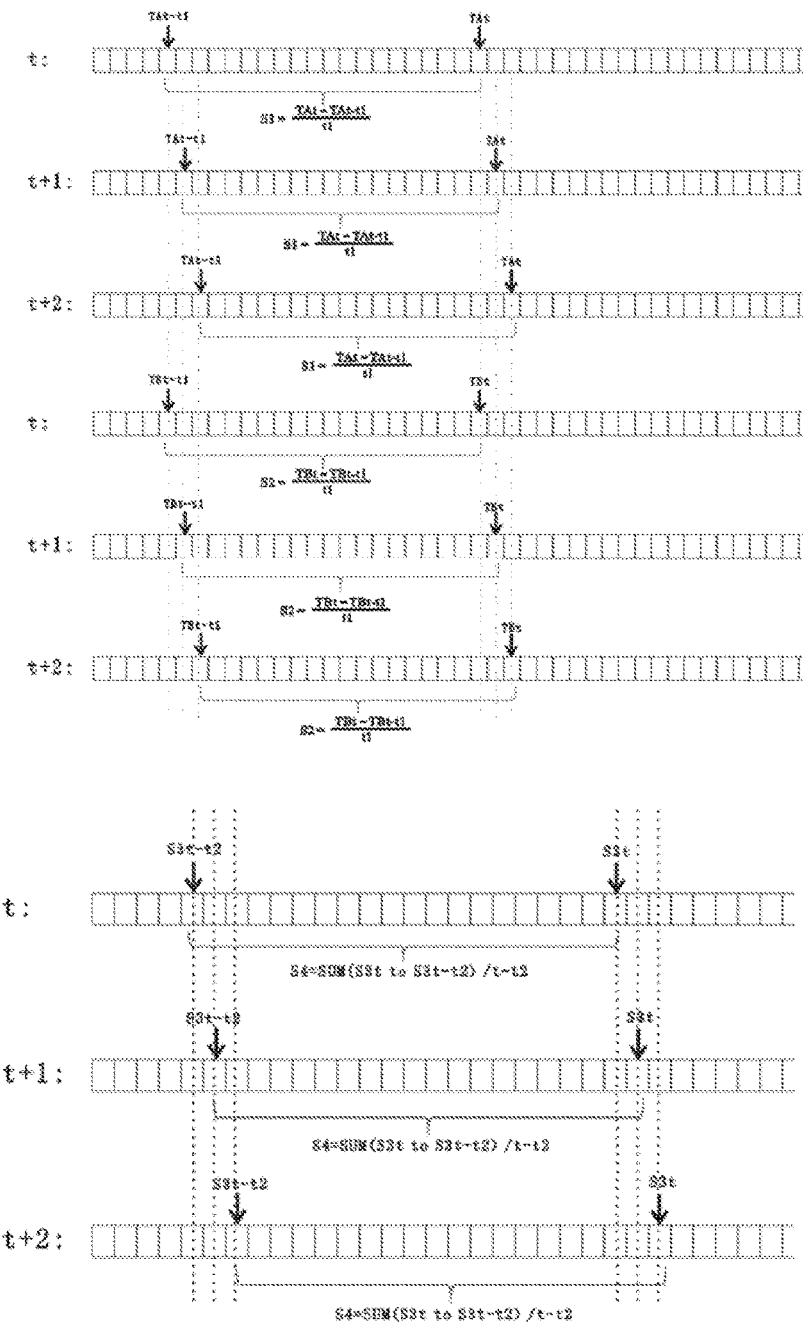

FIG. 4, a flowchart of operations for detecting a wearable device's contact with a living body according to example embodiments of present invention is provided;

FIG. 5 schematically illustrates the calculations performed by the processor by example.

DETAILED DESCRIPTION

In principle, to collect the temperature of body skin, the temperature sensor/probe should always touch the body skin, otherwise the collected temperature data will not be accurate.

However, a human is always in motion such as breathing, turning over even during sleep etc., so it is difficult to ensure the temperature sensor/probe to be always in good contact with the body skin. Thus, it is desirable to be able to detect the state of contact of the temperature sensor/probe in a timely manner, so that a remedial action may be taken when the temperature sensor/probe comes loose, especially in situations such as parenting and health care.

Moreover, as more and more wearable devices come to market with physical properties such as tiny, slim, light weight, etc., which means these wearable devices are easy to lose, however their loss is difficult to be noticed immediately, it is also desirable to be able to detect the wearing state of a wearable device.

In light of the above, it would be desirable to provide a solution for detecting a wearable device's contact with a living body, which can detect whether a wearable device is in contact with a living body accurately, reliably and timely.

Embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being transmitted, received and/or stored in accordance with embodiments of the present invention. Thus, use of any such terms should not be taken to limit the spirit and scope of embodiments of the present invention.

Figure 1:
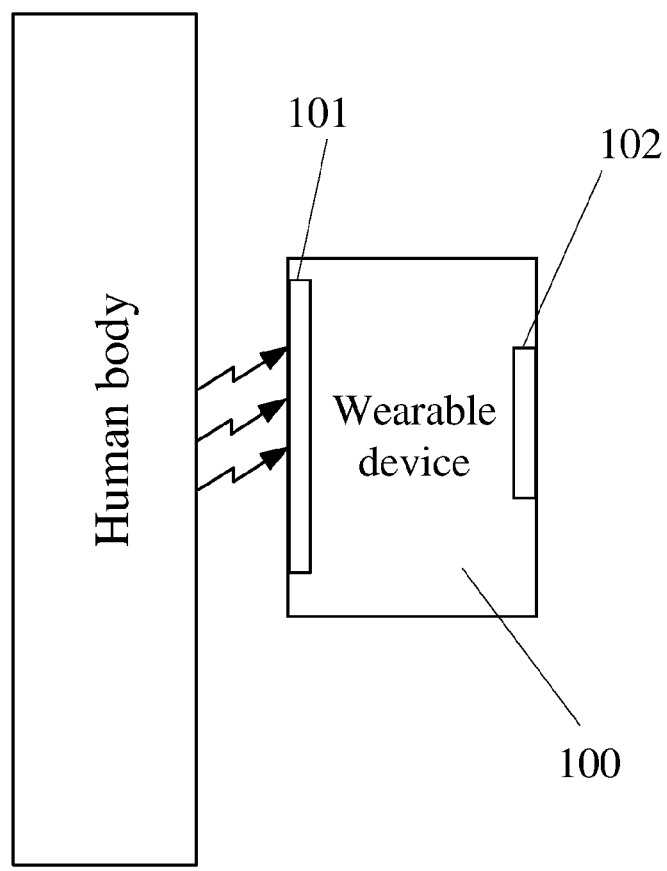
FIG. 1 illustrates an example wearable device which may be used in embodiments of the invention.

Referring now to FIG. 1, an example wearable device 100 which may be used in embodiments of the invention is illustrated. The wearable device 100 may be a wearable thermometer, or any other wearable device comprising temperature sensors, such as a smart watch, smart glasses, smart wrist band, smart bracelet, smart necklace, smart ankle bracelet, smart jewelry, earbud, activity tracker, smart clothing and accessories, wearable health monitoring or health care device, etc. with a temperature measuring function. As shown, the wearable device 100 may be adhered, fixed, stuck, bound, tied or otherwise attached to a living body, such as a human body, and be kept in contact with the skin. The wearable device 100 may be attached to any part of the living body, for example, the chest, abdomen, wrist, etc.

The wearable device 100 may comprise at least two temperature sensors. For example, the wearable device 100 may comprise two temperature sensors, temperature sensor 1 101 and temperature sensor 2 102. Temperature sensor 1 101 may be located at the bottom of the wearable device 100 to touch the skin for detecting the skin temperature, and temperature sensor 2 102 may be located at the top of the wearable device 100 for detecting the environmental temperature. The temperature sensors may be any device or means which may be included in a wearable device and configured to detect temperature. For example, the temperature sensors may be thermostats, thermistors, resistive temperature detectors, thermocouples, or other types of temperature sensors. A thermal insulation layer may be located between these two temperature sensors in order to slow the temperature equilibrium between these two temperature sensors. In other embodiments, the wearable device 100 may comprise any other number of temperature sensors, provided only that both the skin temperature and the ambient temperature may be measured.

In some embodiments, the wearable device 100 may further comprise other components, such as a processor for controlling other components and performing needed processing on data, a memory device for storing data to be processed and instructions configuring the processor. The wearable device 100 may further comprise user interface and controls for receiving user input and presenting information to the user, for example, keys, a display, a speaker, etc. Alternatively or additionally, the wearable device 100 may comprise a wireless communication interface for transmitting data or results of the processing to another computing device for further processing, storage or presenting. Moreover, the wearable device 100 may also comprise other sensors and functional components as needed for its specific functions.

Figure 2:
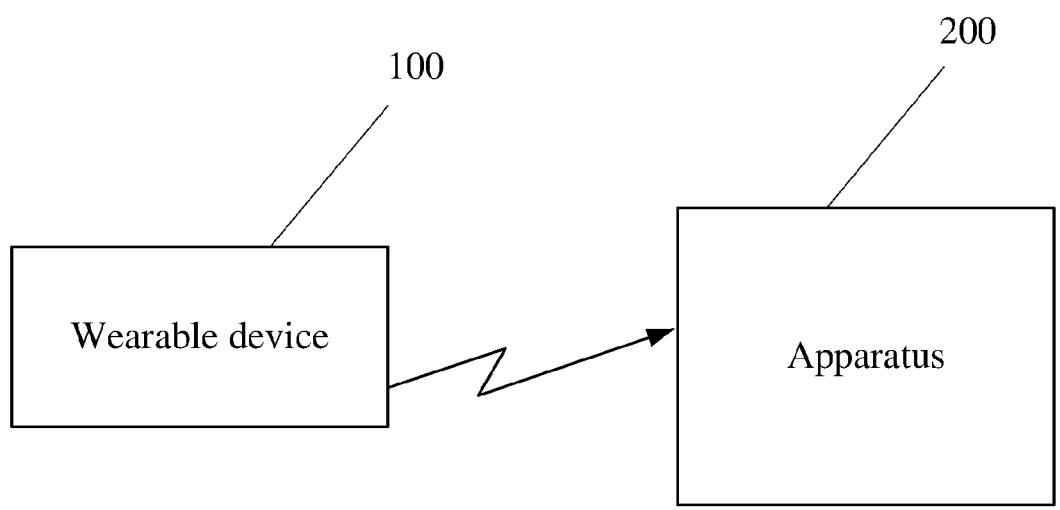
FIG. 2 is a schematic diagram of a system for detecting a wearable device' contact with a living body according to example embodiments of the present invention.

Referring to FIG. 2, a schematic diagram of a system for detecting a wearable device' contact with a living body according to example embodiments of the present invention is provided. As shown, the system comprises the wearable device 100 as shown in FIG. 1 and described above, and an apparatus 200 for detecting the wearable device' contact with a living body according to example embodiments of the present invention.

In example embodiments, the wearable device 100 may be in communication with the apparatus 200 for transmitting data such as temperature data measured by the temperature sensors to the apparatus 200.

In some example embodiments, the wearable device 100 may be configured to communicate wirelessly through its wireless communication interface with the apparatus 200 for transmitting the data. In this regard, the wearable device 100 may be implemented with ultra-low power miniaturized electronic components capable of communicating with the apparatus 200, for example, via a Bluetooth® low energy network, and/or other wireless personal area network (WPAN). The wearable device 100 may also communicate wirelessly with the apparatus 200 via other wireless communication technology such as WiFi.

In these example embodiments, the apparatus 200 may be any computing device or part thereof that may be configured to receive the data from the wearable device 100 via the wireless communication technology, perform the processing as described below on the data, and output the results of the processing, such as presenting to the user. In some embodiments, the apparatus 200 may be a smart mobile device, for example, a smart mobile phone, a tablet computer, etc, or part thereof. The apparatus 200 may be carried by the person who wears the wearable device 100, and thus, the apparatus 200 may be used to process the data transmitted from the wearable device 100 and present the results timely and conveniently to the person. Alternatively, the apparatus 200 may be carried by another person (for example, a parent, health care personnel, etc.) than the one (for example, a child, patient, etc.) who wears the wearable device 100, and thus, the apparatus 200 may be used to process the data transmitted from the wearable device 100 and present the results to the other person, for example, for parenting or health care purposes.

In some other example embodiments, the apparatus 200 may be included in or embodied as the wearable device 100, and thus may receive the data such as temperature data measured by the temperature sensors via internal communication lines, perform the processing as described below on the data, and output the results of the processing, such as presenting to the user through an output interface of the wearable device 10, or sending to another computing device through an wireless communication interface of the wearable device 10.

Figure 3:
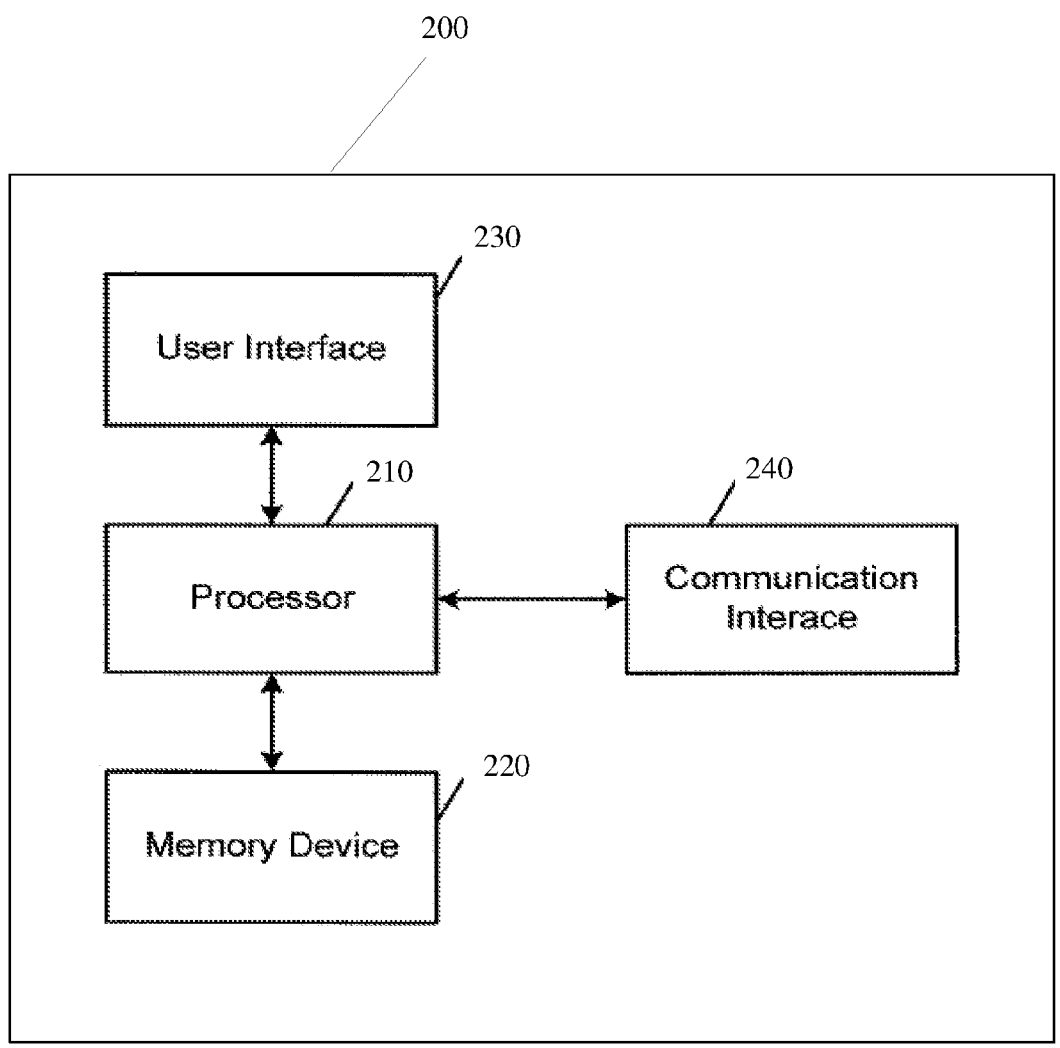
FIG. 3 is a schematic diagram of an apparatus for detecting a wearable device' contact with a living body according to example embodiments of the present invention.

Referring to FIG. 3, a schematic diagram of the apparatus 200 for detecting a wearable device' contact with a living body according to example embodiments of the present invention is provided. Apparatus 200 may comprises at least one processor 210, at least one memory device 220 including computer program code, an optional user interface 230 and/or an optional communication interface 240.

In an example embodiment, the processor 210 (and/or co-processors or any other processing circuitry assisting or otherwise associated with the processor 210) may be in communication with the memory device 220 via a bus for passing information among components of the apparatus 200. The memory device 220 may include, for example, one or more volatile and/or non-volatile memories. In other words, for example, the memory device 220 may be an electronic storage device (for example, a computer readable storage medium) comprising gates configured to store data (for example, bits) that may be retrievable by a machine (for example, a computing device like the processor 210). The memory device 220 may be configured to store information, data, applications, instructions, or the like for enabling the apparatus 200 to carry out various functions in accordance with an example embodiment of the present invention. For example, the memory device 220 could be configured to buffer input data for processing by the processor 210. Additionally or alternatively, the memory device 220 could be configured to store instructions for execution by the processor 210.

The apparatus 200 may be embodied as a chip or chip set. In other words, the apparatus 200 may comprise one or more physical packages (for example, chips) including materials, components and/or wires on a structural assembly (for example, a baseboard). The structural assembly may provide physical strength, conservation of size, and/or limitation of electrical interaction for component circuitry included thereon. The apparatus 200 may therefore, in some cases, be configured to implement an example embodiment of the present invention on a single chip or as a single "system on a chip." As such, in some cases, a chip or chipset may constitute means for performing one or more operations for providing the functionalities described herein.

The processor 210 may be embodied in a number of different ways. For example, the processor 210 may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in an example embodiment, the processor 210 may include one or more processing cores configured to perform independently. A multi-core processor may enable multiprocessing within a single physical package. Additionally or alternatively, the processor 210 may include one or more processors configured in tandem via the bus to enable independent execution of instructions, pipelining and/or multithreading.

In an example embodiment, the processor 210 may be configured to execute instructions stored in the memory device 220 or otherwise accessible to the processor 210. Alternatively or additionally, the processor 210 may be configured to execute hard coded functionality. As such, whether configured by hardware or software methods, or by a combination thereof, the processor 210 may represent an entity (for example, physically embodied in circuitry) capable of performing operations according to an example embodiment of the present invention while configured accordingly. Thus, for example, when the processor 210 is embodied as an ASIC, FPGA or the like, the processor 210 may be specifically configured hardware for conducting the operations described herein. Alternatively, as another example, when the processor 210 is embodied as an executor of software instructions, the instructions may specifically configure the processor 210 to perform the algorithms and/or operations described herein when the instructions are executed. However, in some cases, the processor 210 may be a processor of a specific device (for example, a mobile terminal or network entity) configured to employ an example embodiment of the present invention by further configuration of the processor 210 by instructions for performing the algorithms and/or operations described herein. The processor 210 may include, among other things, a clock, an arithmetic logic unit (ALU) and logic gates configured to support operation of the processor 210.

Meanwhile, the optional communication interface 240 may be any means such as a device or circuitry embodied in either hardware or a combination of hardware and software that is configured to receive and/or transmit data from/to a network and/or any other device or module in communication with the wearable device 100. In this regard, the communication interface 240 may include, for example, an antenna (or multiple antennas) and supporting hardware and/or software for enabling communications with a wireless communication network. Additionally or alternatively, the communication interface 240 may include the circuitry for interacting with the antenna(s) to cause transmission of signals via the antenna(s) or to handle receipt of signals received via the antenna(s). In some environments, the communication interface 240 may alternatively or also support wired communication. As such, for example, the communication interface 240 may include a communication modem and/or other hardware/software for supporting communication via cable, digital subscriber line (DSL), universal serial bus (USB) or other mechanisms.

In an example embodiment, the apparatus 200 may include a user interface 230 that may, in turn, be in communication with the processor 210 to receive an indication of, or relating to, a user input and/or to cause provision of an audible, visual, mechanical or other output to the user. As such, the user interface 230 may include, for example, a keyboard, a mouse, a joystick, a display, a touch screen(s), touch areas, soft keys, a microphone, a speaker, or other input/output mechanisms.

Alternatively or additionally, the processor 210 may comprise user interface circuitry configured to control at least some functions of one or more user interface elements such as, for example, a speaker, ringer, microphone, display, and/or the like. The processor 210 and/or user interface circuitry comprising the processor 210 may be configured to control one or more functions of one or more user interface elements through computer program instructions (for example, software and/or firmware) stored on a memory accessible to the processor 210 (for example, memory device 220, and/or the like).

According to an example embodiment, communication interface 240 may be configured to communicate with a communication interface of the wearable device 100, either directly or over a network 200, for receiving data from the wearable device 100, and/or transmitting data and/or instructions to the wearable device 10.

Referring to FIG. 4, a flowchart of operations for detecting a wearable device's contact with a living body according to example embodiments of present invention is provided. The operations may be performed by the apparatus 200 according to example embodiments of the present invention, or may be performed by a computer program product for detecting a wearable device' contact with a living body according to example embodiments of the present invention, or may constitute steps of a method detecting a wearable device' contact with a living body according to example embodiments of the present invention.

As shown in operation 401, the processor 210 of the apparatus 200 may be configured to obtain a decreasing rate of body temperature and a decreasing rate of environmental temperature measured by the wearable device 100 worn on a living body.

Specifically, the processor 210 may be configured to receive data of body temperatures measured across a first unit time interval by the temperature sensor 1 101 of the wearable device 100, and data of environmental temperatures measured across the first unit time interval by the temperature sensor 2 102 of the wearable device 100 from the wearable device 100, and then calculate a decreasing rate of body temperature by dividing the difference between the body temperatures across the first unit time interval by the length of the first unit time interval, and calculate a decreasing rate of environmental temperature by dividing the difference between the environmental temperatures across the first unit time interval by the length of the first unit time interval.

Alternatively, the wearable device 100 (specifically, for example, its processor) may calculate a decreasing rate of body temperature based on the measured body temperatures across the first unit time interval and a decreasing rate of environmental temperature based on the measured environmental temperatures itself, and then send the calculated decreasing rate of body temperature and the decreasing rate of environmental temperature to the apparatus 200 to be received by the processor 210 of the apparatus 200.

The first unit time interval may be set in advance by the processor 210 of apparatus 200 or the wearable device 100 as any appropriate time period value. For example, in an embodiment, the first unit time interval may be set as about 2 minutes, or 60 samples at a sample rate of 2 seconds.

In example embodiments, the wearable device 100 may be configured to measure the body temperature and the environmental temperature successively via its temperature sensor 1 101 and temperature sensor 2 102 respectively, and send the data of the measured body temperature and the environmental temperature or the calculated decreasing rate of body temperature and the decreasing rate of environmental temperature successively to the apparatus 200. Correspondingly, the processor 201 of the apparatus 200 may calculate or obtain the decreasing rate of body temperature and the decreasing rate of environmental temperature successively.

For example, the temperature sensor 1 101 and the temperature sensor 2 102 of the wearable device 100 may measure the body temperature and the environmental temperature respectively at a specific sample rate, for example, 2 seconds, and send the data of the measured body temperature and environmental temperature to the apparatus 200 or the processor of the wearable device 100 successively. The processor 210 of the apparatus 200 or the processor of the wearable device 100 may take the data of the measured body temperature and measured environmental temperature across every first unit time interval, for example, about 2 minutes (for example, about 60 samples at a sample rate of 2 seconds), and calculate the decreasing rate of the body temperature and the decreasing rate of the environmental temperature across every first unit time interval successively. That is, for example, at a sample rate of 2 seconds, and with the first unit time interval of 60 samples, the processor may take each body temperature sample or environmental temperature sample, calculate the decrease of this temperature sample relative to the previous temperature sample 60 samples apart, and divide this decrease by 60, so as to obtain the decreasing rate of the temperature.

Referring back to FIG. 4, as shown in operation 402, the processor 210 of the apparatus 200 may be further configured to determine the wearable device's contact with the living body based on a comparison of the decreasing rate of body temperature and the decreasing rate of environmental temperature.

Specifically, the processor 210 of the apparatus 200 may be configured to determine that the wearable device is not in good contact with the living body when the decreasing rate of body temperature is greater than the decreasing rate of environmental temperature.

For example, the processor 210 may be configured to determine that the wearable device is not in good contact with the living body when the decreasing rate of body temperature is greater than the decreasing rate of environmental temperature by a preset threshold. The threshold may be obtained from experiments and set in advance in the apparatus 200. In an example, the threshold may be set as 0.02 degree Celcius.

Specifically, in some embodiments, the processor 210 may be configured to calculate a difference between the decreasing rate of body temperature and the decreasing rate of environmental temperature successively, calculate a moving average of the difference between the decreasing rate of body temperate and the decreasing rate of environmental temperature in a second unit time interval; and then determine that the wearable device is not in good contact with the living body when the moving average is greater than the preset threshold.

For example, for each pair of a decreasing rate of body temperature and a decreasing rate of environmental temperature calculated for each pair of a body temperature sample and an environmental temperature sample in the above operation 401, the processor 210 may calculate a difference between this pair of a decreasing rate of body temperature and a decreasing rate of a body temperature, then calculate a moving average of this difference between the pair of decreasing rates in a second unit time interval. The second unit time interval may be set in the apparatus 200 in advance as any time value, for example, about 0.6 minutes, or 20 samples at a sample rate of 2 seconds, in which case the processor 201 will calculate the moving average of the differences between pairs of decreasing rates in each unit time interval of 20 samples. When the moving average is greater than the preset threshold, the processor 201 may determine that the wearable device is not in good contact with the living body.

FIG. 5 schematically illustrates the calculations performed by the processor 201 by example. As shown, at each point in time t, the processor 201 calculates the difference between the body temperature sample TAt at this point in time t and the body temperature sample TAt-t1 at the previous point in time t-t1, with t1 being the first unit time interval. A point in time may be expressed by a sample position in the sample sequence, and the first unit time interval may be expressed by a number of successive samples. Then, the processor 201 calculates the decreasing rate of body temperature by dividing the difference by the length of the first unit time interval at each point in time successively:

$$S1 = \frac{TAt - TAt-t1}{t1}$$

In the same way, the processor 201 calculates the decreasing rate of environmental temperature at each point in time successively:

$$S2 = \frac{TBt - TBt - t1}{t1}$$

Next, the processor 201 calculates the difference between the decreasing rate of body temperature and the decreasing rate of environmental temperate at each point in time successively, S3=S1−S2. Then, the processor 201 calculates a moving average of the difference in a second unit time interval at each point in time t2 successively:

S4=SUM(S3t to S3t−t2)/t−t2

A pseudo code is provided below to further illustrate the above calculations performed by the processor 201:
Set TA=T_sensor1 TB=T_sensor2
Set t1=60/*the unit interval which is about 2 minutes since the experimental thermometer samples every 2 seconds*/

$$\text{Set } S1 = \frac{TAt - TA(t-t1)}{t1}$$

/*which is the changing rate of TA in the unit interval*/

$$\text{Set } S2 = \frac{TBt - TB(t-t1)}{t1}$$

/*which is the changing rate of TB in the unit interval*/
Set S3=S1−S2/*which is to calculate the difference between S1 and S2*/
Set t2=20/*the unit interval which is about 0.6 minutes*/

$$\text{Set } S4 = \frac{S3t + S3(t-1) + S3(t-2) + S3(t-3) \ldots + S3(t-t2)}{t2}$$

/*which is to calculate the moving average of S3*/
IF (S1<0) AND (S2<0) THEN Return S4
ELSE Return 0
Set $S_{MIN}$=−0.02/*threshold which could be obtained from experiment*/
IF S4<$S_{MIN}$ THEN Return RESULT="Loose"

In some embodiments, in addition to the determination performed in the operation 402, optionally the processor 201 may be further configured to determine that the wearable device is not in good contact with the living body when the decreasing rate of body temperature and the decreasing rate of environmental temperature are equal, and that the body temperature and the environmental temperature are also equal. This operation is directed to a situation where the wearable device has come loose from the living body for a long time, so the measured body temperature and environmental temperature and changing rates thereof both tend to be equal.

Referring back to FIG. 4, as shown in operation 403, the processor 210 of the apparatus 200 may be further configured to raise an alarm when determining that the wearable device is not in good contact with the living body. The alarm may be raised via any means, such as visual, audio, vibration, etc, which may be provided in the apparatus 200. For example, when the apparatus 200 is embodied by a mobile device, the processor 210 may control the speaker of the mobile device to produce a particular sound, or control the vibration means to produce a vibration, etc. By raising the alarm, the user may become aware that the wearable device 100 is not in good contact with the living body, and thus may take a remedial action, such as restoring the wearable device 100 to be in good contact with the living body, etc.

Example embodiments of the present invention can realize detecting if a wearable thermometer or other wearable devices is in good contact with a living body, and compared with existing solutions, the detection presented is much more accurate and timely, thus benefiting the user.

As described above, FIG. 4 illustrates a flowchart of an apparatus 202, method, and computer program product for detecting a wearable device' contact with a living body according to example embodiments of the invention. It will be understood that each block of the flowchart, and combinations of blocks in the flowcharts may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory device 220 of an apparatus 200 employing an example embodiment of the present invention and executed by a processor 210 of the apparatus 200. As will be appreciated, any such computer program instructions may be loaded onto a computer or other programmable apparatus (for example, hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowcharts support combinations of means for performing the specified functions and combinations of operations for performing the specified functions for performing the specified functions. It will also be understood that one or more blocks of the flowchart, and combinations of blocks in the flowchart, may be implemented by special purpose hardware-based computer systems which perform the specified functions, or combinations of special purpose hardware and computer instructions.

In an example embodiment, certain ones of the operations above may be modified or further amplified. Furthermore, in an example embodiment, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method comprising:
   obtaining a decreasing rate of body temperature and a decreasing a rate of environmental temperature measured by a wearable device worn on a living body; and
   determining the wearable device's contact with the living body based on a comparison of the decreasing rate of body temperature and the decreasing rate of environmental temperature;
   wherein the determining the wearable device's contact with the living body based on a comparison of the decreasing rate of body temperature and the decreasing rate of environmental temperature comprises:
   determining that the wearable device is not in good contact with the living body when the decreasing rate of body temperature is greater than the decreasing rate of environmental temperature;
   wherein the determining that the wearable device is not in good contact with the living body when the decreasing rate of body temperature is greater than the decreasing rate of environmental temperature comprises:
   determining that the wearable device is not in good contact with the living body when the decreasing rate of body temperature is greater than the decreasing rate of environmental temperature by a preset threshold; and
   wherein the obtaining a decreasing rate of body temperature and a decreasing rate of environmental temperature measured by a wearable device worn on a living body comprises:
   obtaining a decreasing rate of body temperature and a decreasing rate of environmental temperature across a first unit time interval successively; and
   the determining that the wearable device is not in good contact with the living body when the decreasing rate of body temperature is greater than the decreasing rate of environmental temperature by a preset threshold comprises:
   calculating a difference between the decreasing rate of body temperature and the decreasing rate of environmental temperature successively;
   calculating a moving average of the difference between the decreasing rate of body temperate and the decreasing rate of environmental temperature in a second unit time interval; and
   determining that the wearable device is not in good contact with the living body when the moving average is greater than the preset threshold.

2. The method of claim 1, wherein the determining the wearable device's contact with the living body based on a comparison of the decreasing rate of body temperature and the decreasing rate of environmental temperature further comprises:
   determining that the wearable device is not in good contact with the living body when the decreasing rate of body temperature and the decreasing rate of environmental temperature are equal, and that the body temperature and the environmental temperature are also equal.

3. The method of claim 1, further comprising:
   raising an alarm when determining that the wearable device is not in good contact with the living body.

4. An apparatus comprising at least one processor; and
   at least one memory including computer program code;
   the at least one memory and the computer program code configured to, with the at least one processor, cause the apparatus at least to:
   obtain a decreasing rate of body temperature and a decreasing a rate of environmental temperature measured by a wearable device worn on a living body; and
   determine the wearable device's contact with the living body based on a comparison of the decreasing rate of body temperature and the decreasing rate of environmental temperature;
   wherein the at least one memory and the computer program code configured to, with the at least one processor, cause the apparatus at least to determine the wearable device's contact with the living body based on a comparison of the decreasing rate of body temperature and the decreasing rate of environmental temperature comprises being configured to cause the apparatus at least to determine that the wearable device is not in good contact with the living body when the decreasing rate of body temperature is greater than the decreasing rate of environmental temperature;
   wherein the at least one memory and the computer program code configured to, with the at least one processor, cause the apparatus at least to determine that the wearable device is not in good contact with the living body when the decreasing rate of body temperature is greater than the decreasing rate of environmental temperature comprises being configured to cause the apparatus at least to determine that the wearable device is not in good contact with the living body when the decreasing rate of body temperature is greater than the decreasing rate of environmental temperature by a preset threshold; and
   wherein the at least one memory and the computer program code configured to, with the at least one processor, cause the apparatus at least to obtain a decreasing rate of body temperature and a decreasing rate of environmental temperature measured by a wearable device worn on a living body comprises being configured to cause the apparatus at least to:
   obtain a decreasing rate of body temperature and a decreasing rate of environmental temperature across a first unit time interval successively; and
   the at least one memory and the computer program code configured to, with the at least one processor, cause the apparatus at least to determine that the wearable device is not in good contact with the living body when the decreasing rate of body temperature is greater than the decreasing rate of environmental temperature by a preset threshold comprises being configured to cause the apparatus at least to:

calculate a difference between the decreasing rate of body temperature and the decreasing rate of environmental temperature successively;

calculate a moving average of the difference between the decreasing rate of body temperate and the decreasing rate of environmental temperature in a second unit time interval; and determine that the wearable device is not in good contact with the living body when the moving average is greater than the preset threshold.

5. The apparatus of claim 4, wherein the at least one memory and the computer program code configured to, with the at least one processor, cause the apparatus at least to determine that the wearable device is not in good contact with the living body when the decreasing rate of body temperature is greater than the decreasing rate of environmental temperature comprises being further configured to cause the apparatus to:

determine that the wearable device is not in good contact with the living body when the decreasing rate of body temperature and the decreasing rate of environmental temperature are equal, and that the body temperature and the environmental temperature are also equal.

6. The apparatus of claim 4, wherein the at least one memory and the computer program code are further configured to, with the at least one processor, cause the apparatus at least to raise an alarm when determining that the wearable device is not in good contact with the living body.

7. The apparatus of claim 4, wherein the apparatus is integrated with the wearable device.

8. The apparatus of claim 4, wherein the apparatus is separate from the wearable device and communicating with the wearable device wirelessly.

9. A wearable device configured to be worn a living body, comprising:

a first temperature sensor configured to measure a body temperature of the living body;

a second temperature sensor configured to measure an environmental temperature of the environment; and the apparatus of claim 4.

10. A computer program product comprising at least one non-transitory computer-readable storage medium having computer-readable program code portions stored therein, the computer-readable program code portions comprising:

a first program code portion configured to obtain a decreasing rate of body temperature and a decreasing a rate of environmental temperature measured by a wearable device worn on a living body; and a second program code portion configured to determine the wearable device's contact with the living body based on a comparison of the decreasing rate of body temperature and the decreasing rate of environmental temperature;

wherein the second program code portion being configured to determine the wearable device's contact with the living body based on a comparison of the decreasing rate of body temperature and the decreasing rate of environmental temperature comprises being configured to:

determine that the wearable device is not in good contact with the living body when the decreasing rate of body temperature is greater than the decreasing rate of environmental temperature;

wherein the second program code portion being configured to determine that the wearable device is not in good contact with the living body when the decreasing rate of body temperature is greater than the decreasing rate of environmental temperature comprises being configured to:

determine that the wearable device is not in good contact with the living body when the decreasing rate of body temperature is greater than the decreasing rate of environmental temperature by a preset threshold; and wherein the first program code portion being configured to obtain a decreasing rate of body temperature and a decreasing rate of environmental temperature measured by a wearable device worn on a living body comprises being configured to:

obtain a decreasing rate of body temperature and a decreasing rate of environmental temperature across a first unit time interval successively; and the second program code portion being configured to determine that the wearable device is not in good contact with the living body when the decreasing rate of body temperature is greater than the decreasing rate of environmental temperature by a preset threshold comprises being configured to:

calculate a difference between the decreasing rate of body temperature and the decreasing rate of environmental temperature successively;

calculate a moving average of the difference between the decreasing rate of body temperate and the decreasing rate of environmental temperature in a second unit time interval; and determine that the wearable device is not in good contact with the living body when the moving average is greater than the preset threshold.

11. The computer program product of claim 10, wherein the second program code portion being configured to determine the wearable device's contact with the living body based on a comparison of the decreasing rate of body temperature and the decreasing rate of environmental temperature comprises being further configured to:

determine that the wearable device is not in good contact with the living body when the decreasing rate of body temperature and the decreasing rate of environmental temperature are equal, and that the body temperature and the environmental temperature are also equal.

12. The computer program product of claim 10, wherein the computer-readable program code portions comprising a third program code portion configured to:

raise an alarm when determining that the wearable device is not in good contact with the living body.

* * * * *